United States Patent [19]

Carlson

[11] Patent Number: 5,126,569
[45] Date of Patent: Jun. 30, 1992

[54] APPARATUS FOR MEASURING OPTICAL PROPERTIES OF MATERIALS

[75] Inventor: Douglas J. Carlson, Boston, Mass.

[73] Assignee: Massachusetts Institute of Technology, Cambridge, Mass.

[21] Appl. No.: 322,098

[22] Filed: Mar. 10, 1989

[51] Int. Cl.$^5$ .......................................... G01N 21/59
[52] U.S. Cl. .................... 250/341; 250/330; 356/51; 356/432; 358/107; 358/113
[58] Field of Search ............... 250/330, 341; 356/432, 356/51, 443; 358/113, 107

[56] References Cited

U.S. PATENT DOCUMENTS

| 3,767,304 | 10/1973 | Keenan et al. | 356/432 |
| 4,673,807 | 7/1987 | Kobayashi et al. | 356/443 |
| 4,887,155 | 12/1989 | Massen | 358/107 |

FOREIGN PATENT DOCUMENTS

| 2907790 | 9/1980 | Fed. Rep. of Germany . |
| 0508760 | 1/1977 | U.S.S.R. . |
| 0656133 | 4/1979 | U.S.S.R. . |
| 0669301 | 7/1979 | U.S.S.R. . |
| 0811128 | 3/1981 | U.S.S.R. . |
| 1000945 | 2/1983 | U.S.S.R. . |
| 1112316 | 9/1984 | U.S.S.R. . |

OTHER PUBLICATIONS

Preshy et al., "Automatic Refractive-Index Profiling of Optical Fibers", Applied Optics, 17 (14), Jul. 1978, pp. 2209-2218.
Beltrame et al., "ACTA:Automated Image Analysis for Absorption, Fluorescence and Phase Contrast Studies of Cell Images", Conf. IEEE 1980 Frontiers of Engineering in Health Care, Wash., D.C., Sep. 28-30, 1980, pp. 58-60.
Jastrezebski et al., J. Appl. Phys. 51:2301 (1980), "Determination of Carrier Concentration & Compensation Microprofiles in GaAs".
Sherman et al., Applied Optics 9(4):802 (1970), "Scanned Laser Infrared Microscope".
Jungbluth et al., Solid State Comm. 13:1099 (1973), "Scanning Laser Infrared Microscopy of Doping Inhomogeneities in InAs Single Crystals".
Hayakawa et al., Jpn, J. Appl. Phys. 22(6):1069 (1983), "Spreading Resistance of InSb Crystals Pulled Under Ultrasonic Vibrations".
Frank, et al., Solid State Electronics 10:727 (1967), "Measurement of Diffusion Profile of Zn in n-Type GaAs by a Spreading Resistance Technique".
Queirolo, J. Electrochem. Soc. 125 (10):1672 (1978), "Spreading Resistance Measurements on Gallium Arsenide".

Primary Examiner—Carolyn E. Fields
Attorney, Agent, or Firm—Fish & Richardson

[57] ABSTRACT

Apparatus for measuring an optical property of a sample including a source of radiation for exposing the sample to radiation of a predetermined wavelength; a detector for detecting the light intensity transmitted through the sample as a result of the exposure to generate a transmitted light intensity signal; circuitry for digitizing the transmitted light intensity signal; and an analyzer for determining the optical property from the digitized light intensity.

22 Claims, 3 Drawing Sheets

APPARATUS FOR MEASURING OPTICAL PROPERTIES OF MATERIALS

BACKGROUND OF THE INVENTION

This invention was funded by the U.S. government under a DARPA/Air Force contract no. F33615-83-C-5089. Accordingly, the government has rights in this invention.

This invention relates to measuring optical properties of materials.

The optical properties of a material reveal useful information about the material. For example, the absorption coefficient of a semiconductor is related to the distribution of free charge carriers in the semiconductor. This distribution affects both the yield and performance of fabricated semiconductor devices. Moreover, because the charge carrier distribution is related to dopant concentration levels in the semiconductor, knowledge of its value is necessary in order to determine the degree of chemical perfection achieved during semiconductor growth and to optimize dopant segregation during the growth process.

SUMMARY OF THE INVENTION

In one aspect, the invention features apparatus for measuring an optical property of a sample that includes a source of radiation for exposing the sample to radiation of a predetermined wavelength, a detector for detecting the light intensity transmitted through the sample as a result of the exposure to generate a transmitted light intensity signal, circuitry for digitizing the transmitted light intensity signal, and an analyzer for determining the optical property of interest from the digitized light intensity.

In preferred embodiments, the detector includes a video camera (preferably equipped with a silicon-vidicon tube) and the analyzer includes a digital computer. The preferred sample is a semiconductor and the preferred optical properties are absorption coefficient and index of refraction. The radiation source preferably is adapted to expose the sample to radiation in the near-infrared region (about 0.7–4 µm). The transmitted light intensity signal preferably is digitized to form a 512×512 pixel image having 8-bit resolution.

The invention also features a process for measuring the optical property of a sample. Where the sample is a semiconductor and the optical property being measured is the absorption coefficient, the charge carrier distribution and distribution of EL2 sites throughout the sample can be determined from the absorption coefficient. EL2 sites are a type of mid-gap defect.

In a second aspect, the invention features apparatus for quantitatively determining the charge carrier distribution throughout a semiconductor sample. The apparatus includes a source of radiation for exposing a series of locations throughout the sample to near-infrared radiation, a detector for detecting the light intensity transmitted through each of the locations to generate a transmitted light intensity signal, and an analyzer for determining the charge carrier distribution from the transmitted light intensity signal. Preferably, the detector includes a video camera equipped with a silicon-vidicon tube. The analyzer preferably determines the charge carrier distribution using the following relationship:

$$\log_{10} n = \frac{1}{a}(\log_{10}\alpha + b)$$

where n, α, a, and b are as defined in the description of the preferred embodiments.

The invention also features a process for quantitatively determining the charge carrier distribution throughout a semiconductor sample that includes the steps of measuring the absorption coefficient of the sample in the near-infrared region at a series of locations throughout the sample, determining the charge carrier concentration at each of these locations from the absorption coefficient values, and determining the charge carrier distribution from the distribution of these charge carrier concentration values throughout the sample.

In a third aspect, the invention features apparatus for measuring the absorption coefficient of a semiconductor sample that includes a source of radiation for exposing the sample to near infrared radiation; a detector for detecting the light intensity transmitted through the sample as a result of the exposure to generate a transmitted light intensity signal; circuitry for digitizing the transmitted light intensity signal; and an analyzer for determining the absorption coefficient from the digitized light intensity. Preferably, the analyzer determines the absorption coefficient using the relationship $$\exp(\alpha d) = \frac{(1-R)^2}{2T}\left\{1 + \left[1 + \frac{4R^2 T^2}{(1-R)^4}\right]^{\frac{1}{2}}\right\}$$

where α, d, R, and T are as defined in the description of the preferred embodiments.

The invention provides a simple, accurate, and rapid means of measuring the optical properties of a material. Conventional optical arrangements and silicon-based imaging devices can be used. In the case of charge carrier distribution measurements, spatial resolution to less than one micron can be achieved.

Other features and advantages of the invention will be apparent from the following description of the preferred embodiments thereof and from the claims.

DESCRIPTION OF THE PREFERRED EMBODIMENTS

We first describe the figures.

USE

Figure 1:
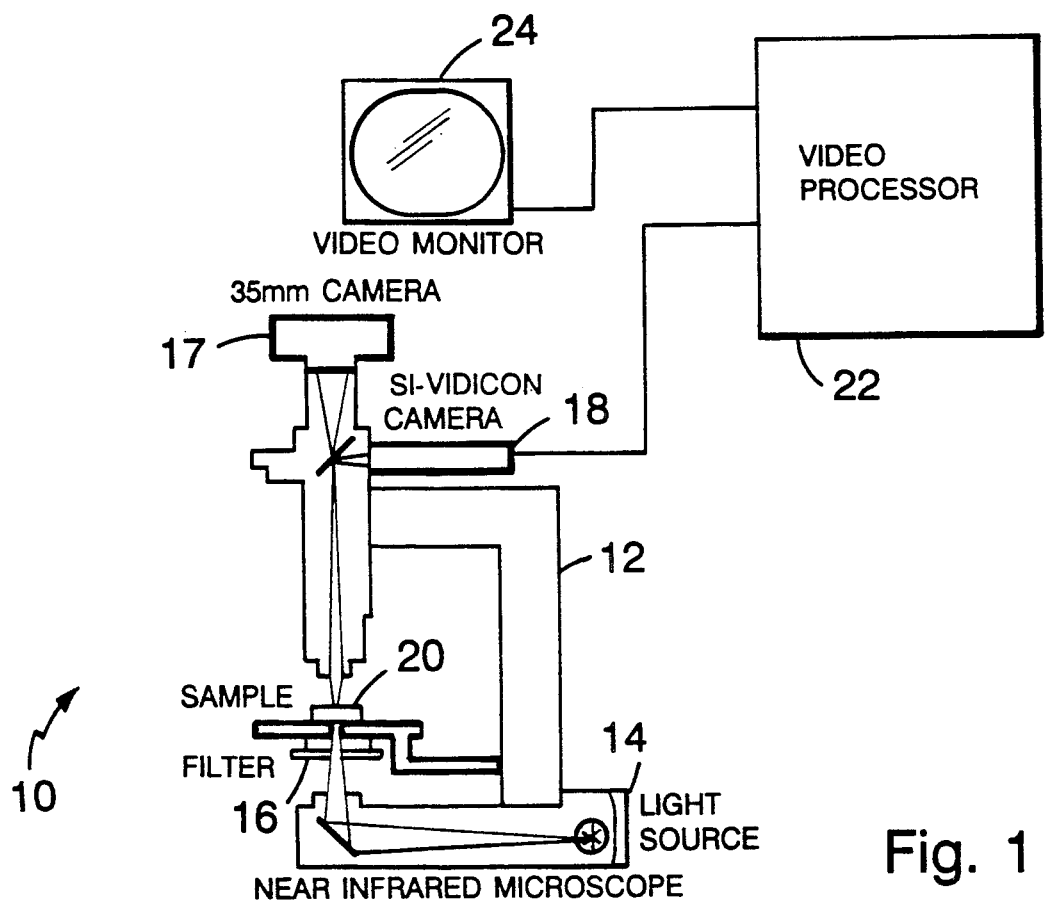
FIG. 1 is a schematic drawing of apparatus for measuring the charge carrier distribution of a semiconductor sample.

Referring to FIG. 1, apparatus 10 features a standard transmission optical microscope 12 (e.g., a Zeiss Axiotron microscope) equipped with an infrared light source 14 and a narrow band pass filter 16 for confining the wavelength of illumination to about 1 µm (which places it in the near infrared region). Microscope 12 is further fitted with a 35 mm camera (17) and an extended red silicon or lead sulfide vidicon camera 18 for detecting the optical signal transmitted through semiconductor sample 20 (e.g., a gallium arsenide wafer) when it is exposed to radiation from light source 14.

Camera 18 outputs a standard RS-170 video signal to a computer-based video processing system 22, e.g., a Recognition Technology, Inc. image processing system resident in a MASSCOMP MC5500 computer. Video processing system 22 digitizes the incoming video signal into a 512×512 pixel image with 8-bit (256 gray level) intensity resolution. Thus, the intensity of light transmitted through sample 20 at any point and detected by camera 18 is transformed, in real time, into a digitized light intensity value available for computational analysis. System 22 also stores and processes the digitized data (as described below) to obtain the desired optical information (e.g., absorption coefficient, charge carrier distribution, etc.) and then re-converts it to an analog signal for display on a video monitor 24.

Operation

Figure 2:
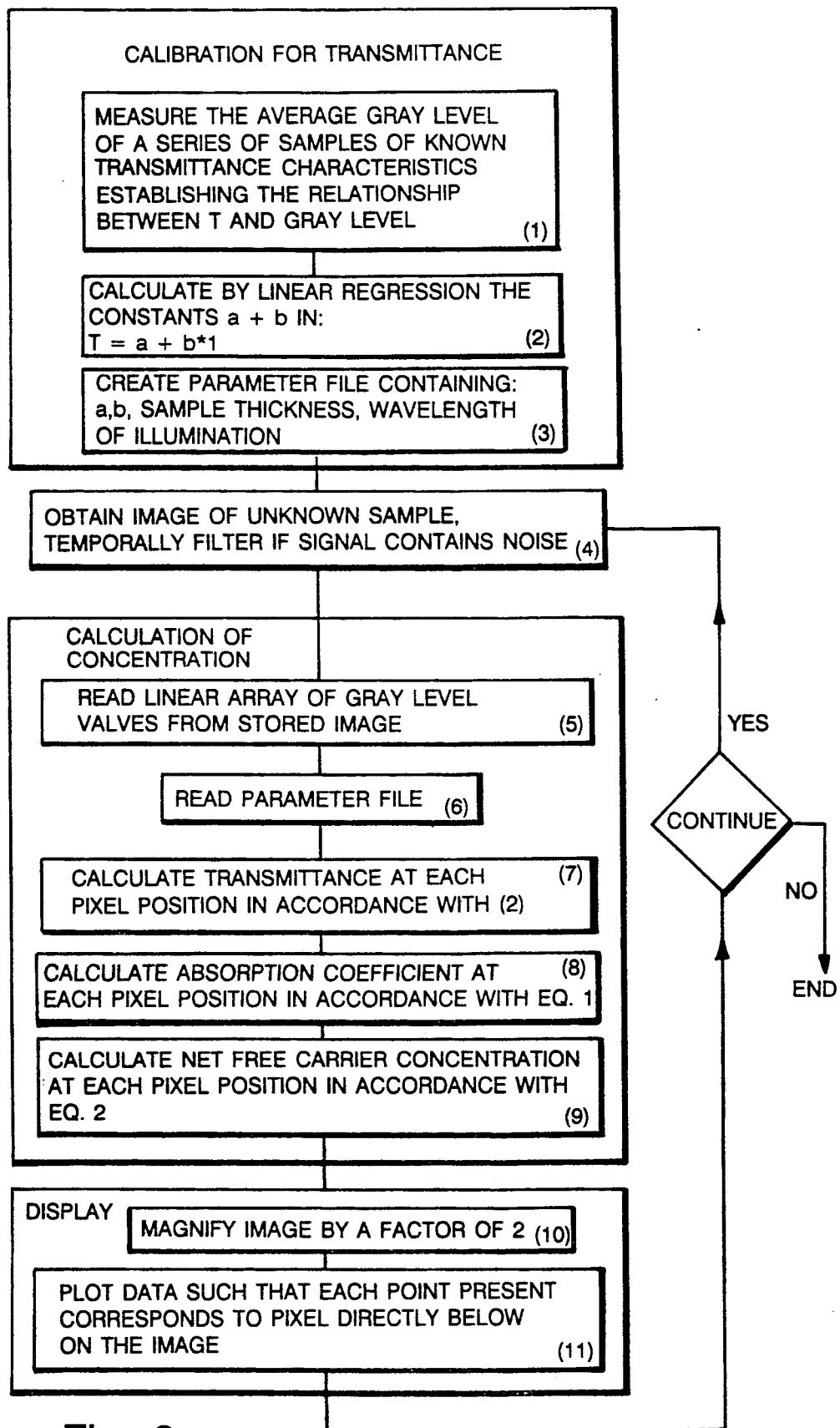
FIG. 2 is a flow chart describing the determination of the net free charge carrier distribution in a semiconductor sample.

Referring to FIG. 2, the first step in determining the net free charge carrier distribution in an n-type gallium arsenide sample is a calibration run to correlate gray level (i.e. digitized light intensity value) with transmittance (1). To accomplish this, a series of gallium arsenide samples having known transmittance values are placed in microscope 12 and illuminated at a wavelength of about 1 μm (as determined by band pass filter 16). The resulting light intensity signal detected by camera 18 is digitized by video processing system 22 and the average gray level values of each image are calculated. These gray level values are equated to the bulk transmittance values of the calibration samples, thereby establishing a correlation between detected gray level value from the sample and transmittance. This data is then used as input to a linear regression subroutine which calculates the constants necessary to convert gray level to transmittance in a sample of unknown transmittance (2).

Once the correlation between gray level and transmittance has been established, video processing system 22 is calibrated for the measurement of transmittance at the selected wavelength (1 μm) and with the selected optics (Zeiss Axiotron microscope equipped with silicon-vidicon camera). This calibration data, along with the wavelength of illumination, sample thickness, graphical display instructions, and the calibration data establishing the gray level-transmittance correlation are placed in a parameter file for use by the program in calculating the free charge carrier concentration and determining the display characteristics for displaying the final data on video monitor 24 (3). Apparatus 10 is now ready to analyze a gallium arsenide sample of unknown transmittance.

The sample is placed in microscope 12 and its top surface is illuminated with near infrared radiation from light source 14. The transmitted optical signal from the sample is detected by camera 18, which converts the signal to a standard RS-170 video signal and inputs this video signal to video processing system 22.

Video processing system 22 digitizes the incoming video signal and stores the digitized image. If the level of noise in the video signal is high and a stable image cannot be obtained, system 22 applies temporal averaging to improve image quality (4). Next, a user-defined linear array of gray level values is read from the stored image (5) and transformed into transmittance values (7) using the correlation between gray level and transmittance established in the previous calibration step (6).

Once the transmittance values have been obtained, they are converted to absorption coefficients (8) using the following equation:

$$\exp(\alpha d) = \frac{(1-R)^2}{2T} \left\{ 1 + \left[ 1 + \frac{4R^2 T^2}{(1-R)^4} \right]^{\frac{1}{2}} \right\} \quad (1)$$

where $\alpha$ is the absorption coefficient, d is the length of the optical path through the sample (which is equal to the thickness of the sample), T is the transmittance, and R is the reflection coefficient. Values of R as a function of the wavelength of illumination have been tabulated and are listed in Seraphin and Bennet, *Semiconductors and Semimetals*, Vol. 3, ch. 12, ed. Willardson and Beer (Academic - New York) (1975). For a wavelength of 1.0 μm, R=0.3098.

From the absorption coefficient values, the net free charge carrier concentration is calculated at each pixel position (9) according to the following equation:

$$\log_{10} n = \frac{1}{a} (\log_{10} \alpha + b) \quad (2)$$

where n is the free charge carrier concentration, $\alpha$ is the absorption coefficient, and a and b are constants determined in a separate calibration step using samples of known free charge carrier concentration and absorption coefficient at the wavelength of interest. Values of a and b for illumination wavelengths between 1 and 2 μm are set forth in the following table:

| λ (μm) | a | b | Correlation Coefficient |
| --- | --- | --- | --- |
| 1.0 | 0.282 | 4.29 | 0.99 |
| 1.05 | 0.322 | 5.04 | 0.99 |
| 1.1 | 0.395 | 5.58 | 0.99 |
| 1.5 | 0.669 | 10.61 | 0.98 |
| 1.8 | 0.669 | 11.40 | 0.98 |
| 2.0 | 0.652 | 11.08 | 0.98 |

The net free charge carrier distribution is then determined from the distribution of charge carrier concentration values throughout the sample.

Figure 3:
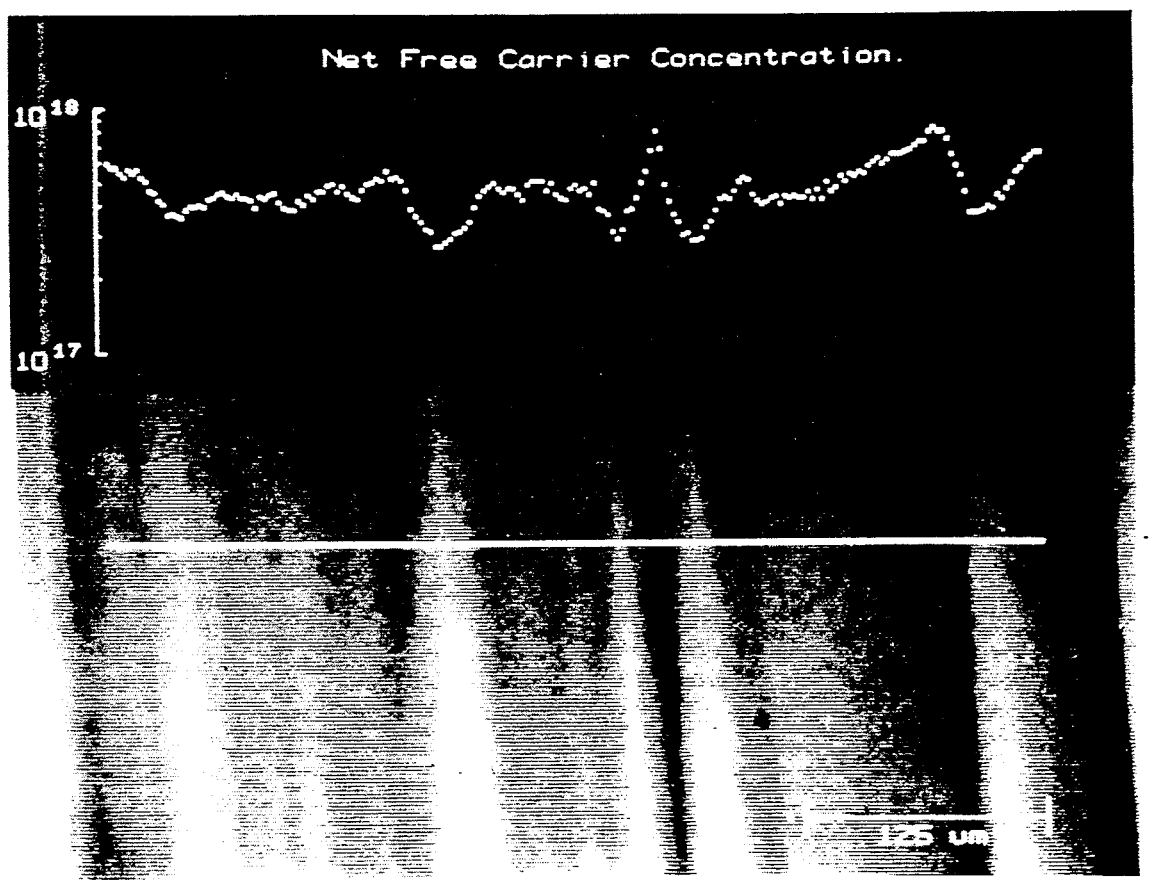
FIG. 3 is a visual representation of the net free charge carrier distribution in a semiconductor sample.

To visualize the charge carrier distribution data, it is presented on video monitor 24 in the form of a split screen, as shown in FIG. 3. One half of the screen contains a plot of the charge carrier concentration vs. distance while the other half of the screen displays the near infrared micrograph with a line indicating the pixel array analyzed (11). To facilitate viewing, the near infrared micrograph is magnified by a factor of two (10) by turning off the interlacing of the video image, copying the image to another image storage unit, and then reactivating the interlacing. The entire sample analysis takes less than five seconds.

Other embodiments are within the following claims.

For example, apparatus 10 can also be used in determining the micro and macrodistribution of EL2 sites throughout a sample and for ion implant analyses.

Apparatus 10 can also be used to measure the refractive index of the sample.

I claim:

1. Apparatus for measuring an optical property of a sample, or a property derivable therefrom, comprising a source of radiation for exposing said sample to radiation of a predetermined wavelength;

a video camera for detecting the light intensity transmitted through said sample as a result of said exposure to generate a transmitted light intensity signal;

circuitry for digitizing the transmitted light intensity signal and determining the transmittance of said sample from the digitized light intensity signal; and an analyzer for determining the optical property, or a property derivable therefrom, from said transmittance.

2. The apparatus of claim 1 wherein said video camera is equipped with a silicon-vidicon tube.

3. The apparatus of claim 1 wherein said radiation is near-infrared radiation.

4. The apparatus of claim 1 wherein said analyzer comprises a digital computer.

5. The apparatus of claim 1 wherein the optical property comprises the index of refraction.

6. The apparatus of claim 1 wherein said circuitry digitizes said transmitted light intensity signal into a $512 \times 512$ pixel image.

7. The apparatus of claim 6 wherein said image has 8-bit intensity resolution.

8. Apparatus for measuring the absorption coefficient of a sample, or a property derivable therefrom, comprising a source of radiation for exposing said sample to radiation of a predetermined wavelength;

a video camera for detecting the light intensity transmitted through said sample as a result of said exposure to generate a transmitted light intensity signal;

circuitry for digitizing the transmitted light intensity signal; and an analyzer for determining the absorption coefficient, or a property derivable therefrom, from the digitized light intensity.

9. A process for measuring an optical property of a sample, or a property derivable therefrom, comprising the steps of exposing said sample to a source of radiation;

detecting the light intensity transmitted through said sample as a result of said exposure step with a video camera and generating a transmitted light intensity signal therefrom;

digitizing the transmitted light intensity signal;

determining the transmittance of said sample from the digitized light intensity signal; and determining the optical property, or a property derivable therefrom, from said transmittance.

10. The process of claim 9 wherein said optical property is the absorption coefficient.

11. The process of claim 10 wherein said sample is a semiconductor and said process further comprises the step of determining the charge carrier distribution throughout said sample from said absorption coefficient.

12. The process of claim 10 wherein said sample is a semiconductor and said process further comprises the step of determining the distribution of EL2 sites throughout said sample from said absorption coefficient.

13. The process of claim 9 wherein said optical property is the index of refraction.

14. The process of claim 9 wherein said sample comprises a semiconductor.

15. The process of claim 9 wherein said radiation is near-infrared radiation.

16. The process of claim 9 wherein said video camera is equipped with a silicon-vidicon tube.

17. Apparatus for quantitatively determining the charge carrier distribution throughout a semiconductor sample comprising a source of radiation for exposing a series of locations throughout said sample to near-infrared radiation;

a detector for detecting the light intensity transmitted through each of said locations to generate a transmitted light intensity signal; and an analyzer for determining said charge carrier distribution from said transmitted light intensity signal.

18. The apparatus of claim 17 wherein said detector comprises a video camera equipped with a silicon-vidicon tube.

19. The apparatus of claim 17 wherein said analyzer determines said charge carrier distribution using the relationship $$log_{10}n = 1/a(log_{10}\alpha + b)$$

where n is the free charge carrier concentration, $\alpha$ is the absorption coefficient, and a and b are constants determined in a separate calibration step using samples of known free charge carrier concentration and absorption coefficient at the wavelength of interest.

20. A process for quantitatively determining the charge carrier distribution throughout a semiconductor sample comprising the steps of measuring the absorption coefficient of said sample in the near-infrared region at a series of locations throughout said sample;

determining the charge carrier concentration at each of said locations from said absorption coefficient values; and determining said charge carrier distribution from the distribution of said charge carrier concentration values throughout said sample.

21. Apparatus for measuring the absorption coefficient of a semiconductor sample comprising a source of radiation for exposing said sample to near-infrared radiation;

a video camera for detecting the light intensity transmitted through said sample as a result of the exposure to generate a transmitted light intensity signal;

circuitry for digitizing said transmitted light intensity signal; and an analyzer for determining said absorption coefficient from the digitized light intensity.

22. The apparatus of claim 21 wherein said analyzer determines said absorption coefficient using the relationship $$exp(\alpha d) = (1-R)^2/2T\{1 + [1 + (4R^2T^2)/(1-R)^4]^{\frac{1}{2}}\}$$

where $\alpha$ is the absorption coefficient, d is the length of the optical path through the sample (which is equal to the thickness of the sample), T is the transmittance, and R is the reflection coefficient.

* * * * *